United States Patent
Chen et al.

(10) Patent No.: US 6,187,907 B1
(45) Date of Patent: Feb. 13, 2001

(54) TRIPLE HELIX COIL TEMPLATE HAVING A BIOLOGICALLY ACTIVE LIGAND

(76) Inventors: James Chen, 44 Dunnigan Dr., Pomona, NY (US) 10970; Li-An Yeh, 27 Samuel Dr., N. Grafton, MA (US) 01536

( * ) Notice: Under 35 U.S.C. 154(b), the term of this patent shall be extended for 0 days.

(21) Appl. No.: 09/144,419

(22) Filed: Aug. 31, 1998

(51) Int. Cl.[7] .............................. C07K 2/00; C07K 14/78
(52) U.S. Cl. ...................... 530/345; 530/356; 530/402
(58) Field of Search .................................. 530/300, 345, 530/350, 356, 402, 408, 409, 410, 411; 514/2, 8, 12, 21

(56) References Cited

U.S. PATENT DOCUMENTS

| | | | |
|---|---|---|---|
| 5,114,953 | 5/1992 | Galardy et al. | 514/323 |
| 5,576,419 | * 11/1996 | Fields | 530/322 |
| 5,856,308 | * 1/1999 | St. Pierce | 514/18 |

OTHER PUBLICATIONS

Dawson et al., "Convenient Total Synthesis of a 4–Helix TASP Molecule by Chemoselective Ligation", J. Am. Chem. Soc., 115:7263–7266 (1993).

Tuchscherer et al., "The TASP Concept: Mimetics of Peptide Ligands Protein Surfaces and Folding Units", Tetrahedron, 49(17):3559–3575 (1993).

Alberg et al., "Structure–Based Design of a Cyclophilin–Calcineuren Bridging Ligand", Science, 262:248–250 (Oct. 8, 1993).

Garcia et al., "Three Dimensional Structure of an Angiotensin II–Fab Complex at 3 A Hormone Recognition by an Anti–Idiotypic Antibody", Science, 257:502–507 (Jul. 24, 1992).

Lee et al., "Strong Inhibition of Fibrinogen Binding to Platelet Receptor $\alpha IIb\beta 3$ by RGD Sequences Installed into a Presentation Scaffold", Protein Engineering, 6(7):745–754 (1993).

Rypacek, "Polymer–Bound Enzyme Inhibitors: Synthesis, Properties, and Physiological Relevance", Critical Reviews in Therapeutic Drug Carrier Systems, 9(3,4):189–212 (1992).

Grobelny et al., "Inhibition of Human Skin Fibroblast Collagenase, Thermolysin, and *Pseudomonas aeruginosa* elastase by Peptide Hydroxamic Acids", Biochemistry, 31:7152–7154 (1992).

Eyre, "Collagen: Molecular Diversity in the Body's Protein Scaffold", Science, 207:1315–1322 (Mar. 21, 1980).

Attassi et al., "Design of Peptide Enzymes (pepzymes): Surface–Simulation Synthetic Peptides that Mimic the Chymotrypsin and Trypsin Active Sites Exhibit . . . Enzyme", Proc.Natl.Acad.Sci. USA, 90:8282–8286 (Sep. 1993).

Fields et al., Melanoma Cell Adhesion and Spreading Activities of a Synthetic 124–Residue Triple–helical "Mini–collagen", The Journal of Biological Chemistry, 268(19):14153–14160 (1993).

Germann et al., "A Synthetic Model of Collagen: An Experimental Investigation of the Triple–Helix Stability", Biopolymers, 27:157–163 (1988).

Thakur et al., "Influence of Different Tripeptides on the Stability of the Collagen Triple Helix. II. An Experimental Approach with Appropriate Variations . . . Oligotripeptide", Biopolymers, 25:1081–1086 (1986).

Roth et al., "Triple Helix–Coil Transition of Covalently Bridged Collagenlike Peptides", Biopolymers, 19:1909–1917 (1980).

Chen et al., "An Energetic Evaluation of a "Smith " Collagen Microfibril Model", Journal of Protein Chemistry 10(5):535–551 (1991).

* cited by examiner

*Primary Examiner*—Jeffrey E. Russel
(74) *Attorney, Agent, or Firm*—Fish & Richardson P.C.

(57) ABSTRACT

A template-ligand conjugate including (1) a template made of three cross-linked polypeptide chains, wherein the three polypeptide chains each contain tripeptide or hexapeptide repeat sequences aligned to form a triple helix coil; and (2) at least one biologically active ligand attached to the template via covalent bonding with one of the three polypeptide chains.

27 Claims, No Drawings

SEQUENCE LISTING

<160> NUMBER OF SEQ ID NOS: 3

<210> SEQ ID NO 1
<211> LENGTH: 18
<212> TYPE: PRT
<213> ORGANISM: Homo sapiens
<220> FEATURE:
<221> NAME/KEY: VARIANT
<222> LOCATION: (3)...(3)
<223> OTHER INFORMATION: Xaa = hydroxy proline
<221> NAME/KEY: VARIANT
<222> LOCATION: (6)...(6)
<223> OTHER INFORMATION: Xaa = hydroxy proline
<221> NAME/KEY: VARIANT
<222> LOCATION: (9)...(9)
<223> OTHER INFORMATION: Xaa = hydroxy proline
<221> NAME/KEY: VARIANT
<222> LOCATION: (12)...(12)
<223> OTHER INFORMATION: Xaa = hydroxy proline

<400> SEQUENCE: 1

Gly Pro Xaa Gly Pro Xaa Gly Pro Xaa Gly Pro Xaa Gly Pro Pro Ser
 1               5                  10                  15

Gly Gly

<210> SEQ ID NO 2
<211> LENGTH: 20
<212> TYPE: PRT
<213> ORGANISM: Homo sapiens
<220> FEATURE:
<221> NAME/KEY: VARIANT
<222> LOCATION: (1)...(1)
<223> OTHER INFORMATION: Xaa = 6-hydroxyamino-3-methylhexanoyl
<221> NAME/KEY: VARIANT
<222> LOCATION: (5)...(5)
<223> OTHER INFORMATION: Xaa = hydroxy proline
<221> NAME/KEY: VARIANT
<222> LOCATION: (8)...(8)
<223> OTHER INFORMATION: Xaa = hydroxy proline
<221> NAME/KEY: VARIANT
<222> LOCATION: (11)...(11)
<223> OTHER INFORMATION: Xaa = hydroxy proline
<221> NAME/KEY: VARIANT
<222> LOCATION: (14)...(14)
<223> OTHER INFORMATION: Xaa = hydroxy proline

<400> SEQUENCE: 2

Xaa Trp Gly Pro Xaa Gly Pro Xaa Gly Pro Xaa Gly Pro Xaa Gly Pro
 1               5                  10                  15

Pro Ser Gly Gly
            20

<210> SEQ ID NO 3
<211> LENGTH: 7
<212> TYPE: PRT
<213> ORGANISM: Homo sapiens
<220> FEATURE:
<221> NAME/KEY: VARIANT
<222> LOCATION: (5)...(5)
<223> OTHER INFORMATION: Xaa = N-3(2,4-dinitrophenyl)-L-2,3-
     diaminopropionyl

<400> SEQUENCE: 3

Pro Leu Gly Leu Xaa Ala Arg
 1               5

TRIPLE HELIX COIL TEMPLATE HAVING A BIOLOGICALLY ACTIVE LIGAND

BACKGROUND OF THE INVENTION

In general, a therapeutic molecule which targets an enzyme (e.g., collagenase), a receptor (e.g., G protein couple receptor), or an effector (e.g., antibody) must meet two requirements. First, it must contain a template with which one or more biologically active ligands are incorporated. Second, the conformation of the template must be further modified chemically so as to augment the specificity and potency of the therapeutic molecule. Unfortunately, chemical modification typically introduces excessive degrees of freedom into the initial template, thereby decreasing the probability of the interaction between the biologically active ligand and its target.

SUMMARY OF THE INVENTION

The present invention provides a triple helix coil template for presenting one or more biologically active ligands to a target.

More specifically, an aspect of this invention relates to a template-ligand conjugate which includes (1) a template made of three cross-linked polypeptide chains (i.e., covalently crossed-linked via a tri-crosslinker or otherwise), the three polypeptide chains each containing tripeptide or hexapeptide repeat sequences aligned to form a triple helix coil; and (2) at least a biologically active ligand attached to the template via covalent bonding with one of the three polypeptide chains. Preferably, at least a biologically active ligand is covalently bonded to each of the three polypeptide chains.

If the repeat sequences are located in one terminal region (either N- or C-terminal) of each of the three polypeptide chains, it is preferred that at least one biologically active ligand be attached to the terminal amino acid residue in the same terminal region of one polypeptide chain and that each terminal amino acid residue in the opposite region of each polypeptide chains be covalently bonded to a tri-crosslinker. Further, it is preferable that all three polypeptide chains in a template-ligand conjugate of this invention are identical.

As an example of a template-ligand conjugate of this invention, each of the three polypeptide chains may, independently, have repeat tripeptide sequences of the following formula:

$(AA^1\text{-}AA^2\text{-}AA^3)_m$ in which each $AA^1$, independently, is a Gly, or a D- or L-Ala; each $AA^2$, independently, is a D- or L-Pro; each $AA^3$, independently, is a D- or L-Hyp, or a D- or L-Cys; and m is 4–14 or, preferably, is 4–8. Note that the thiol group of a Cys residue of a tripeptide sequence can form a disulfide bond with the thiol group of a Cys residue of another tripeptide sequence. Also, if one of $AA^1$'s, $AA^2$'s and $AA^3$'s is a D-amino acid residue, then all the of others must also be of D-amino acid residues; and vice versa.

As another example of a template-ligand conjugate of this invention, each of the three polypeptide chains may, independently, have repeat hexapeptide sequences of the following formula:

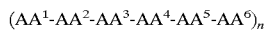
$(AA^1\text{-}AA^2\text{-}AA^3\text{-}AA^4\text{-}AA^5\text{-}AA^6)_n$ wherein each $AA^1$, independently, is a Gly; each $AA^2$, independently, is a D- or L-Pro; each $AA^3$, independently, is a D- or L-Hyp, or a D- or L-Cys; each $AA^4$, independently, is a D- or L-Ala; each $AA^5$, independently, is a D- or L-Pro; each $AA^6$, independently, is a D- or L-Hyp, or a D- or L-Cys; and n is 2–7, or, preferably, 2–4. The thiol group of a Cys residue of a hexapeptide sequence can form a disulfide bond with the thiol group of a Cys residue of another hexapeptide sequence. Also, if one of $AA^1$'s, $AA^2$'s, $AA^3$'s, $AA^4$'s, $AA^5$'s and $AA^6$'s is a D-amino acid residue, then all the of others must also be of D-amino acid residues; and vice versa.

The above-described template has several advantages. For example, the template has a well-defined three-dimensional structure. Thus, a biologically active ligand attached to it can be studied immediately using molecular modeling. Additionally, such a template provides a greater surface region for chemical modifications to increase target specificity and affinity through "multi-domain" binding and to alter any undesirable chemical properties. In addition, a template-ligand conjugate of this invention enables one to reduce the conformational flexibility or entropy of the biologically active ligand in a selective manner. Further, such a conjugate can be used as a substrate-based drug screening tool in lieu of using traditional linear peptide-based combinatorial methods. Finally, a template-ligand conjugate of this invention can also be used in highly specific and efficient columns for the purification of enzymes.

Other features or advantages of the present invention will be apparent from the following detailed description of several embodiments, and also from the appending claims.

DETAILED DESCRIPTION OF THE INVENTION

The present invention relates to a molecule having a template of a covalently crosslinked triple helix coil of three suitable polypeptide chains, each containing tripeptide or hexapeptide repeat sequences, and at least one biologically active ligand attached to the template via covalent bonding with one of the three polypeptide chains (e.g., covalently attached to a terminal or an internal residue of, or bound within, one of the polypeptide chain) without disrupting the triple helix coil. Preferably, the three polypeptide chains are covalently linked to each other via a tri-crosslinker (for example, see below or Goodman, et al., J. Am. Chem. Soc. 118, 5156, 1996). In any event, it is important that the triple helical conformation be maintained when the three polypeptide chains are linked together. Repeat sequences, as defined herein, include a cluster of amino acids which is repeated within a polypeptide chain, preferably forming a substantial portion of the polypeptide chain. Bound within, as defined herein, means that one or more ligands are used in lieu of amino acids within a polypeptide chain of the template. The three polypeptide chains can be identical or can differ by one or more amino acids, and can contain either D- or L-amino acids, or both (herein L-amino acid is intended unless specified). Suitable template-ligand covalent bonds include, for example, normal peptide bonds, modified peptide bonds, or non-peptide bonds. Indeed, each of the polypeptide chains itself may also contain one or more modified peptide bonds or non-peptide bonds.

A biologically active ligand, as defined herein, is a ligand which, when bound to the template, can bind to a target site, such as an enzyme, an effector, or a receptor, to act as an inhibitor, agonist, antagonist or mixed agonist/antagonist. It is also understood that the biologically active ligands also includes physiologically acceptable salts of the ligands. Examples of a suitable biologically active ligands include ligands which inhibit enzymatic action, such as N-[2- isobutyl-3(methoxycarbonyl)-propanoyl]-L-tryptophan, which can be used to inhibit metalloprotease enzymes (e.g., collagenase, gelatinase, and stromelysin). Other suitable ligands include those which bind to receptors, such as an anti-idiotic antibody against Angiotensin II receptor or an Arg-Gly-Asp tripeptide, which, when bound within a polypeptide chain, will also bind to integrin cell surface receptors, thereby inhibiting blood cell adhesion.

One method for synthesizing a template-ligand conjugate of this invention includes synthesizing a triple helix coil template, and then dissolving the template in a suitable solvent such as methanol. A suitable biologically active ligand is then mixed with a reagent, or a combination of reagents, suitable to activate the ligand to support subsequent covalent bonding of the ligand to the template. The activated ligand is then contacted with the template under conditions suitable to support covalent bonding of the ligand to the template.

After reaction, the product is precipitated, for example, by addition of anhydrous ether. The product is then mixed with an hydroxylamine solution to form the composition according to this invention. The syntheses of a composition of this invention is further described in Example 9.

A template-ligand conjugate of this invention can be used to specifically target an enzyme, an effector, or a receptor. For example, it can be used to treat a disease that is induced or exacerbated by one or more enzymes. The conjugate or its pharmaceutically acceptable salt, when used as a therapeutic agent, may be administered either by direct application or by systemic application in an amount predetermined by those of skill in the art.

By bonding a biologically active ligand onto or into a triple helical template, the properties of the ligand, such as solubility and hydrophobicity, can be modified to improve its effectiveness against the target. Further, one can enhance the specific activity of a biologically active ligand by attaching it to a template so as to maintain the ligand in a specific range of collagen-like (triple helical coil) conformations relative to the template's physical configuration. Acceptable specific conformations can be determined by known computational molecular modeling techniques or by NMR.

A template-ligand conjugate of this invention can also be used to assay a sample, such as serum or synovial fluid, for the presence of a specific enzyme, an effector, or a receptor. More specifically, the ligand is first coated, by well-known means such as crosslinking or non-covalent binding, to the surface of a well plate or other suitable container. The sample is then added to the container and incubated to form a complex of the enzyme/effector/receptor and the template-ligand conjugate. The container is subsequently washed with saline to remove the unbound materials in the sample. A monoclonal antibody, which recognizes only the complex is then added. The antibody can be tagged with radioactive iodine or an enzyme, such as horse radish peroxidase, to allow detection. The container is subsequently washed with a suitable solution, such as saline, to remove and excess monoclonal antibody that has not bound to the complex. Finally, the complex can be detected by enzyme-link immunosorbant assay, calorimetric assay, or radioisotope assay for $^{125}$I-linked antibodies.

A template-ligand conjugate of this invention can also be used to purify a sample containing target molecules, such as an enzyme, an effector, or a receptor, in a sample. The conjugate is first fixed to a chemically inert support, such as beads of agarose or sepharose, or an acrylamide natural solid phase support. The sample is then directed past the conjugate fixed on the support. At least a portion of the target molecules in the sample temporarily bind to the ligand, while the non-target portion of the sample typically does not bind to the ligand, thereby separating the target molecules from the sample.

Without further elaboration, it is believed that the above description has adequately enabled the present invention. The following specific examples are, therefore, to be construed as merely illustrative, and not limitative of the remainder of the disclosure in any way whatsoever. All parts and percentages are by weight unless otherwise stated. Also, all of the publications cited herein, including patents, are hereby incorporated by reference in their entirety.

EXAMPLE 1

The structural formulas of a linear template (LT), three non-helical templates having three linked peptide chains (NHT1, NHT2, and NHT3), and a triple helical template (THT) are shown below:

Linear template (LT)
(Gly-Pro-Hyp)$_4$-Gly-Pro-Pro-Ser-Gly-Gly-NH$_2$ (SEQ ID NO:1)

Non-helical template 1 (NHT1)
(Gly-Pro-Hyp)$_1$-Gly-Pro-Pro-Ser-Gly-Gly-Acp⎯⎯⎯⎤
(Gly-Pro-Hyp)$_1$-Gly-Pro-Pro-Ser-Gly-Gly-Acp-Lys-Lys-Gly-NH$_2$
(Gly-Pro-Hyp)$_1$-Gly-Pro-Pro-Ser-Gly-Gly-Acp⎯⎯⎯⎦

Non-helical template 2 (NHT2)
(Gly-Pro-Hyp)$_2$-Gly-Pro-Pro-Ser-Gly-Gly-Acp⎯⎯⎯⎤
(Gly-Pro-Hyp)$_2$-Gly-Pro-Pro-Ser-Gly-Gly-Acp-Lys-Lys-Gly-NH$_2$
(Gly-Pro-Hyp)$_2$-Gly-Pro-Pro-Ser-Gly-Gly-Acp⎯⎯⎯⎦

Non-helical template 3 (NHT3)
(Gly-Pro-Hyp)$_3$-Gly-Pro-Pro-Ser-Gly-Gly-Acp⎯⎯⎯⎤
(Gly-Pro-Hyp)$_3$-Gly-Pro-Pro-Ser-Gly-Gly-Acp-Lys-Lys-Gly-NH$_2$
(Gly-Pro-Hyp)$_3$-Gly-Pro-Pro-Ser-Gly-Gly-Acp⎯⎯⎯⎦

Triple helical template 3 (THT)
(Gly-Pro-Hyp)$_4$-Gly-Pro-Pro-Ser-Gly-Gly-Acp⎯⎯⎯⎤
(Gly-Pro-Hyp)$_4$-Gly-Pro-Pro-Ser-Gly-Gly-Acp-Lys-Lys-Gly-NH$_2$
(Gly-Pro-Hyp)$_4$-Gly-Pro-Pro-Ser-Gly-Gly-Acp⎯⎯⎯⎦

In the above formulas, Hyp and Acp stand for amino acid residues hydroxyproline and ε-amino-caproic acid, respectively, and Gly-NH$_2$ stands for amidated glycine residue (i.e., —NH—CH$_2$—CO·NH$_2$). Of note, the (Acp)-(Lys(Acp)-Lys(Acp)-(Gly)-NH2) moiety served as a tri-crosslinker to link together all three polypeptide chains in each of NHT1, NHT1, and NHT1, and THT; as shown above (e.g., the structure of THT), the carboxyl groups of the 3 Acp residues of the tri-crosslinker moiety reacted respectively with the side chain amino groups of two Lys residues and the terminal amino group of one of the two Lys residues to form 3 amide bonds. Also note that the number of the (Gly-Pro-Hyp) tripeptide repeat sequences in the THT template is 4 (as compared with 1, 2, and 3 for NHT1, NHT2, and NHT3), thereby forming a triple helical coil.

The above-described templates were assembled by stepwise solid-phase procedures on a 4-methylbenzhydrylamine resin (substitution=0.65 mmole/gram). For lysine, the backbone amine groups were protected by fluorenylmethyloxycarbonyl (Fmoc), while the side chain amine groups were protected by either Fmoc or t-butyloxycarbonyl (t-Boc). All other amino acids were protected by t-Boc. Side chain protecting groups of t-Boc-amino acids were benzyl for serine and hydroxyproline. General procedures for peptide synthesis involved standard coupling, as known in the art, using 1 equivalent of protected amino acid with 4 equivalents of N-hydroxybenzotriazole, 4 equivalents of O-benzotriazole-N,N,N',N'-tetramethyl-uranium-hexafluoro-phosphate and 8 equivalents of diisopropylethylamine at room temperature for one hour. After coupling, the coupled amino acid was then deprotected and reacted with an additional protected amino acid. This coupling/deprotection sequence was repeated until the template was fully synthesized. Amino acids protected with a t-Boc group were deprotected with 30% trifluoroacetic acid (TFA) in $CH_2Cl_2$ for 20 minutes. The deprotection of amino acids with Fmoc protecting groups was carried out by 20% piperidine in dimethylformamide for 20 minutes. The peptides were cleaved from the resin with removal of the side-chain protecting group by anhydrous HF-anisol (10:1) at 0° C. for 1 hour and then washed with ether 5 times followed by extraction with 30% acetic acid and lyophilization. The crude peptide was purified by C-18 reversed phase high performance liquid chromatography (HPLC) with 0.1% TFA in water as buffer A and 0.075% TFA in acetonitrile as buffer B. The desired fractions were collected and lyophilized followed by the mass spectral analysis.

D,L-2-isobutyl-3-(methoxycarbonyl)-propanoic acid was synthesized according to the method described in Example 1 of U.S. Pat. No. 5,114,953, issued to Galardy et al. The D,L-2-isobutyl-3-(methoxycarbonyl)-propanoic acid was then treated with 1.02 equivalents of N-hydroxysuccinimide and 1.02 equivalents of dicycloexylcarbodiimide (DCC) at 25° C. for two hours followed by the addition of 1.0 equivalents of L-tryptophan. The reaction mixture was then stirred at room temperature, while the pH was maintained at 8 by the addition of triethylamine to form a mixture of R and S isomers of N-[2-isobutyl-3(methoxycarbonyl)-propanoyl)]-L-tryptophan. The completion of the reaction was monitored by HPLC. The reaction product was then purified by flash chromatography (silica gel) to isomers R and S of the mammalian matrix metalloprotease inhibitor N-[2-isobutyl-3-(methoxycarbonyl)-propanoyl]-L-tryptophan. The R isomer of this biologically active ligand (Ligand A) was used herein to prepare various template-ligand conjugates.

The following is the structural formula of non-helical template 1-ligand conjugate (NHT1-L), in which i-Bu stands for isobutyl:

NHT1-L was prepared as follows:

Ligand A (150 mg; 0.4 mmol), N-hydroxysuccinimide (60 mg; 0.522 mmol) and DCC (101 mg; 0.49 mmol) were stirred in 4 ml of acetonitrile at room temperature for 2 hours. Dicyclohexylurea formed was removed by filtration and rinsed with about I ml of acetonitrile.

NHT1 was dissolved in 2 ml of methanol. The activated ester was added to this solution followed by 100 $\mu$l of triethylamine. The resultant solution was stirred at room temperature overnight, about 17 hours, to form a methyl ester-ligand-template complex.

After reaction, the product complex was precipitated by addition of anhydrous ether. The solution was centrifuged and decanted. The product complex was resuspended in ether, vortexed, centrifuged and decanted one more time. The residue was dried in vacuum.

A hydroxylamine in methanol solution was prepared by mixing a warm solution of KOH (0.88 g per 4 ml methanol) and a warm solution of hydroxylamine hydrochloride (0.736 g in 4 ml methanol) to form a white cloudy solution. This solution was then placed on ice for 10 minutes and centrifuged. The supernatant (hydroxylamine solution) was then used in the subsequent reaction.

To the residue was added 1 ml of the supernatant hydroxylamine solution. The reaction mixture was stirred at room temperature for 7 hours to convert the methyl ester of the ligand moiety to a hydroxamate. At the completion of the reaction, the solvent was removed on a rotary evaporator. The residue was then taken up in 1 ml of water and extracted with ether (3×2 ml). The aqueous layer was then lyophilized to form NHT1-L.

Shown below are the structural formulas of non-helical template 2-ligand conjugate (NHT2-L), non-helical template 3-ligand conjugate (NHT3-L), triple helical template-ligand conjugate (THT-L), and linear template-ligand (LT-L):

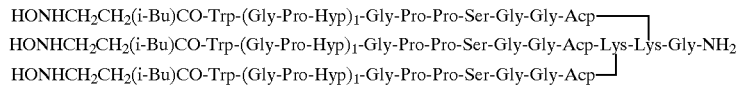

HONHCH$_2$CH$_2$(i-Bu)CO-Trp-(Gly-Pro-Hyp)$_1$-Gly-Pro-Pro-Ser-Gly-Gly-Acp⎤
HONHCH$_2$CH$_2$(i-Bu)CO-Trp-(Gly-Pro-Hyp)$_1$-Gly-Pro-Pro-Ser-Gly-Gly-Acp-Lys-Lys-Gly-NH$_2$
HONHCH$_2$CH$_2$(i-Bu)CO-Trp-(Gly-Pro-Hyp)$_1$-Gly-Pro-Pro-Ser-Gly-Gly-Acp⎦

Non-helical template 2-ligand conjugate (NHT2-L)

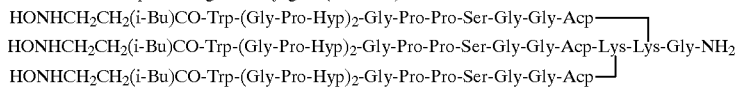

HONHCH$_2$CH$_2$(i-Bu)CO-Trp-(Gly-Pro-Hyp)$_2$-Gly-Pro-Pro-Ser-Gly-Gly-Acp⎤
HONHCH$_2$CH$_2$(i-Bu)CO-Trp-(Gly-Pro-Hyp)$_2$-Gly-Pro-Pro-Ser-Gly-Gly-Acp-Lys-Lys-Gly-NH$_2$
HONHCH$_2$CH$_2$(i-Bu)CO-Trp-(Gly-Pro-Hyp)$_2$-Gly-Pro-Pro-Ser-Gly-Gly-Acp⎦

Non-helical template 3-ligand conjugate (NHT3-L)

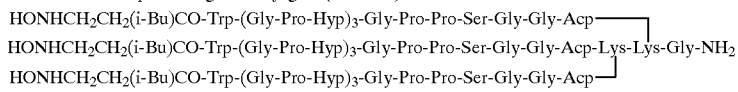

HONHCH$_2$CH$_2$(i-Bu)CO-Trp-(Gly-Pro-Hyp)$_3$-Gly-Pro-Pro-Ser-Gly-Gly-Acp⎤
HONHCH$_2$CH$_2$(i-Bu)CO-Trp-(Gly-Pro-Hyp)$_3$-Gly-Pro-Pro-Ser-Gly-Gly-Acp-Lys-Lys-Gly-NH$_2$
HONHCH$_2$CH$_2$(i-Bu)CO-Trp-(Gly-Pro-Hyp)$_3$-Gly-Pro-Pro-Ser-Gly-Gly-Acp⎦

-continued

Triple helical template-ligand conjugate (THT-L)

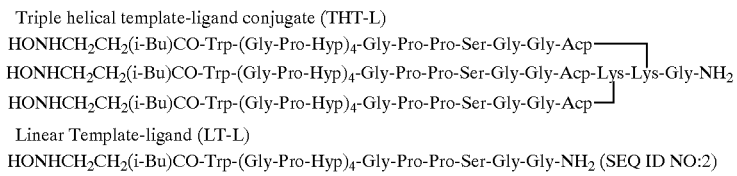

HONHCH₂CH₂(i-Bu)CO-Trp-(Gly-Pro-Hyp)₄-Gly-Pro-Pro-Ser-Gly-Gly-Acp⎤
HONHCH₂CH₂(i-Bu)CO-Trp-(Gly-Pro-Hyp)₄-Gly-Pro-Pro-Ser-Gly-Gly-Acp-Lys-Lys-Gly-NH₂
HONHCH₂CH₂(i-Bu)CO-Trp-(Gly-Pro-Hyp)₄-Gly-Pro-Pro-Ser-Gly-Gly-Acp⎦

Linear Template-ligand (LT-L)

HONHCH₂CH₂(i-Bu)CO-Trp-(Gly-Pro-Hyp)₄-Gly-Pro-Pro-Ser-Gly-Gly-NH₂ (SEQ ID NO:2)

All of the above described template-ligand conjugates were synthesized in a manner analogous to that in which NHT1-L was prepared.

The template-ligand conjugates thus prepared were subjected to analysis by thin layer chromatography. They all showed positive stain with ferric ion (hydroxymate) and Cl₂ tolidine (peptide). Further, they did not move on silica gel when developed with methanol, whereas most impurities did.

To study the inhibitory activity of each of the above-described template-ligand conjugates against activated human interstitial collagenase, an enzyme assay was performed as follows:

Human interstitial collagenase was activated with trypsin as follows. A reaction mixture was prepared in Tris buffer (pH 7.5) containing 20 mM Tris-HCl, 0.15 N NaCl, 4 μg/ml trypsin, 6 nM collagenase and 5 mM CaCl₂. The reaction mixture was incubated at 37° C. for 45 minutes and then soybean trypsin inhibitor was added at 44 μg/ml to quench the reaction.

Various concentrations of each of the template-ligand conjugates were incubated with the activated collagenase for 5 minutes before the addition of the substrate Mca-[Pro-Leu-Gly-Leu-Dpa-Ala-Arg-NH₂] (SEQ ID NO: 3)(Mca stands for 7-methoxycoumarin-4-yl and Dpa stands for N-3-(2,4-dinitrophenyl)-L-2,3-diaminopropionyl). The substrate was added at final 10 μM and was then further incubated at 37° C. for 45 minutes. The reaction was terminated by the addition of 750 μl of 0.1 N sodium acetate buffer (pH 4.0). The hydrolysis of the substrate was assessed by fluorescence, excitation at 328 nm and emission of 393 nm, with a Perkin-Elmer Fluorimeter LS-50B. The IC₅₀ values (in nM) for NHT1-L, NHT2-L, NHT3-L, LT-L, and THT-L are 67, 116, 288, 1400, and 9, respectively. It was unexpected that THT-L showed an inhibitory activity much higher than NHT1-L, NHT2-L, NHT3-L, and LT-L.

EXAMPLE 2

NHT1-L, NHT2-L, NHT3-L, and THT-L were obtained in the same manner as described in Example 1, supra, and then subjected to the following enzyme assay.

Stromelysin was activated with trypsin as set forth below: A reaction mixture was prepared in Tris buffer (pH 7.5) containing 20 mM Tris-HCl, 0.15 N NaCl, 4 μg/ml trypsin, 30 nM stromelysin and 3 mM CaCl₂. The reaction mixture was incubated at 37° C. for 45 minutes and then soybean trypsin inhibitor was added at 44 μg/ml to quench the reaction.

Various concentrations of each of the template-ligand conjugates were incubated with the activated stromelysin for 5 minutes before the addition of the substrate Mca-[Pro-Leu-Gly-Leu-Dpa-Ala-Arg-NH₂](SEQ ID NO: 3). The substrate was added at final 5 μM and was then further incubated at 37° C. for 60 minutes. The reaction was terminated by the addition of 750 μl of 0.1 N sodium acetate buffer (pH 4.0). The hydrolysis of the substrate was assessed by fluorescence, excitation at 328 nm and emission of 393 nm, with a Perkin-Elmer Fluorimeter LS-50B. The IC₅₀ values (in nM) for NHT1-L, NHT2-L, NHT3-L, and THT-L are 240, 287, 1137, and 32, respectively. THT-L showed an unexpectedly low IC₅₀ value, as compared with those for the other three conjugates.

EXAMPLE 3

NHT1-L, NHT2-L, NHT3-L, and THT-L were obtained in the same manner as described in Example 1, supra, and then subjected to the following enzyme assay.

Human gelatinase was activated with trypsin as follows. A reaction mixture was prepared in Tris buffer (pH 7.5) containing 20 mM Tris-HCl, 0.15 N NaCl, 4 μg/ml trypsin, 3 nM gelatinase and 5 mM CaCl₂. The reaction mixture was incubated at 37° C. for 60 minutes and then soybean trypsin inhibitor was added at 44 μg/ml to quench the reaction.

Various concentrations of each of NHT1-L, NHT2-L, NHT3-L, and THT-L were incubated with the activated gelatinase for 5 minutes before the addition of the substrate Mca-[Pro-Leu-Gly-Leu-Dpa-Ala-Arg-NH₂](SEQ ID NO: 3). The substrate was added at final 10 μM and was then further incubated at 37° C. for 60 minutes. The reaction was terminated by the addition of 750 μl of 0.1 N sodium acetate buffer (pH 4.0). The hydrolysis of the substrate was assessed by fluorescence, excitation at 328 nm and emission of 393 nm, with a Perkin-Elmer Fluorimeter LS-50B. The IC₅₀ values (in nM) for NHT1-L, NHT2-L, NHT3-L, and THT-L are 2.3, 24, 52, and <1.0, respectively. The IC₅₀ value for THT-L is unexpectedly low, as compared with those for the other three conjugates.

EXAMPLE 4

The ability of NHT1-L, NHT2-L, NHT3-L, and THT-L, prepared in the same manner as described in Example 1, supra, to inhibit breakdown of the proteoglycan matrix of bone collagen cells (chondrocytes) was assessed by testing for the inhibition of ³⁵S-glycosaminoglycan (³⁵S-GAG) release measured using cartilage explants (3.5 mm diameter×1.0 mm thick) prepared from bovine radiocarpal joints.

Knee joints from a 1 to 3 week old calf were obtained immediately after sacrifice from the Abattoir and then transported on ice. The intact joints were washed with tap water and then soaked in 50% (v/v) Povidine iodine solution, obtained from Barre National, Inc., Baltimore, Md., on ice until dissection. All subsequent steps were performed in a laminar flow tissue culture hood using standard sterile technique. The joint was immobilized in a shank holder and the joint capsule was cut open to expose the articular cartilage using a #21 scalpel. Cartilage explant plugs, approximately 15 mg wet weight, were removed from the flat articulating surfaces in the lower-most region of the knee joint using a sterile steel cork-borer (3.5 mm diameter) and collected in a 250 ml roller bottle containing about 100 ml fresh medium (Delbecco's minimum essential medium (DMEM), obtained from Gibco BRC, LIFE Technologies, Gaithersburg, Md., containing 4.5 g/L D-glucose and L-glutamine (no sodium pyruvate), Hepes and sodium bicarbonate buffers (pH 7.4)) which was supplemented just before use with 100 units penicillin, 100 µg streptomycin and 50 µg L-ascorbic acid per ml of medium.

The explant plugs were cultured in fresh DMEM containing about 10 µCi/ml of $^{35}$S-sodium sulfate for 2 days, while supplied with 5% $CO_2$ and 95% air, to promote incorporation of $^{35}$S sulfate into the proteoglycans of the explants. The explants were then incubated for three days in DMEM without $^{35}SO^{-2}_4$. The DMEM was then replaced with fresh DMEM and the explant plugs were subsequently incubated for one day in the presence of recombinant human Interluken-1α (rhIL-1α) (5 ng/ml) which was introduced to cause matrix degradation, and various concentrations of different template-ligand conjugates between 1–100 µM, after which the $^{35}$S radiation levels, from the $^{35}$S-GAG released into the medium, were determined by scintillation counting.

Each plug was then digested with 250 µl formic acid at 65–70° C. for 4–6 hours, after which a 50 µl aliquot of the digestion mixture was removed for counting. rhIL-α was a negative control. The percentage $^{35}$S-GAG released from each explant was calculated from the formula:

$$\% \text{ release} = \{(cpm_{medium})/(cpm_{medium} + 2cpm_{explant})\} \times 100\%.$$

Among all the template-ligand conjugates tested, THT-L showed much better inhibitory effect than the others, with a dose of 100 µM resulting in an inhibition level of about 90%.

EXAMPLE 5

THT-L, synthesized by the procedures described in Example 1, supra, was tested for its ability to inhibit extracellular matrix degradation in a primary bovine chondrocyte culture as follows:

Two 1 to 3 week old calf radio-carpal joints were obtained immediately after sacrifice from the Abattoir and then transported on ice. The intact joints were washed carefully with a suitable anti-microbial soap, such as HIBICLENS, rinsed clean with distilled, deionized water, and then sequentially rinsed with 50% (v/v) Povidine iodine solution and with 70% ethanol.

All subsequent steps were performed in a laminar flow tissue culture hood using standard sterile technique. The joint was immobilized in a shank holder and the joint capsule cut open to expose the articular cartilage using a #21 scalpel. Using toothed forceps and a #15 scalpel, the cartilage was removed in full thickness pieces from the condyles without cutting deeply into the subchondral bone. The cartilage slices were rinsed sequentially with 25 ml of Delbeccols phosphate buffered saline (D-PBS), supplemented with 1% antibiotic solution (penicillin, streptomycin and fungizone), and then rinsed twice with 25 ml of D-PBS without antibiotics.

The cartilage slices were then digested in 10 ml of an enzymatic digestion solution containing 1 mg/ml of hyaluronidase in serum-free 1:1 DMEM/Ham's F-12 (DMEM/Fl2) for 30 minutes at 37° C. to remove residual hyaluronic acid from the surface of the cartilage slices. All enzyme solutions were 0.22 µm filter sterilized and kept on ice until ready to use. The enzymatic digestion solution was subsequently aspirated. The cartilage slices were rinsed with 25 ml of D-PBS and then digested with 10 ml of a digestion solution, containing 2.5 mg trypsin (from 2.5% 10x liquid diluted 1:10; 1% antibiotic solution) and 2 mg collagenase P per ml serum-free DMEM/Fl2 for 30 minutes and rinsed with saline, to remove the synovial fibroblasts and any adherent connective tissue from the surface of the chips. Finally, the slices were digested with 40 ml of a digestion solution containing 2 mg of bacterial collagenase per ml serum-free DMEM/Fl2 for 6 hours at 37° C. in a BELLCO magnetic cell culture stirring flask, at which point the articular cartilage matrix was fully digested away liberating the chondrocytes.

Undigested tissue was recovered by filtration through a 70 µm nylon mesh strainer and the chondrocytes were collected by centrifugation at 1000×g for 10 minutes at room temperature. The cells were then resuspended in 40 ml of DMEM/Fl2 supplemented with 10% fetal bovine serum and an aliquot of the cells were quantitated in the Coulter counter. Chondrocytes were seeded at a density of $8 \times 10^4$ cells in 0.5 ml DMEM/Fl2 supplemented with 10% fetal bovine serum, in 24-well tissue culture plates and incubated for 4 days in a 37° C. humidified, 5% $CO_2$, 95% air atmosphere. The cultures were again fed on days 4, 7, 11, 14, 18 & 21 with 0.5 ml well of DMEM/Fl2 plus 10% fetal bovine serum.

On day 22, the chondrocyte cultures were rinsed twice with 1 ml of D-PBS and incubated with 0.5 ml/well of DMEM/Fl2 plus 10 uCi $^{35}SO_4^{-2}$ for 48 hours at 37° C. On day 24, the radiolabel-containing media was removed and the cultures re-fed with 0.5 ml/well of DMEM/Fl2 plus 10% fetal bovine serum. The cultures were incubated with media containing non-radioactive $SO_4$-2 for two days to allow incorporation of radiolabel molecules into the extracellular matrix and on day 26 were again fed with 0.5 ml of fresh DMEM/Fl2 plus 10% bovine serum.

On day 27 of the chondrocyte culture formation, the cultures were rinsed twice with 1 ml of D-PBS and incubated for 24 hours with 0.5 ml/well of serum-free DMEM/Fl2 plus 1 ng/ml of human, rhIL-1α and various concentrations of THT-L in triplicate. rhIL-1α was used as the negative control. At 24 hours, the cell layer was rinsed with 1 ml of D-PBS and digested with 0.5 ml of 1×trypsin-EDTA by incubation at 30° C. for 1 hour, and then the $^{35}$S radiolabel was quantitated by scintillation counting. The results of these assays show that THT-L is a far more effective inhibitor than is the acid form of the identical inhibitor with no attached triple helical coil (i.e., N-[2-isobutyl-3-(N'-hydroxycarbonylamido)-propanoyl]-L-tryptophan, which was synthesized as described in Example 14 of U.S. Pat. No. 5,114,953, issued to Galardy et al.). The results also show that the potency of THT-L is similar to that shown by N-[D,L-2-isobutyl-3-(N'-hydroxycarbonylamido)-propanoyl]-tryptophan methylamide, which was synthesized as described in Example 1 of U.S. Pat. No. 5,114,953, issued to Galardy et al. and the R-isomer was separated from the Sisomer by flash chromatography (silica gel, ethyl acetate).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Furthermore, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A template-ligand conjugate comprising:
a template made of three cross-linked polypeptide chains, wherein the three polypeptide chains each contain tripeptide or hexapeptide repeat sequences aligned to form a triple helix coil; and
a first biologically active ligand attached to the template via covalent bonding with one of the three polypeptide chains, wherein the first biologically active ligand does not contribute to the triple helix coil formed by the template.

2. The template-ligand conjugate of claim 1, wherein the repeat sequences are located in the N-terminal region of each of the three polypeptide chains.

3. The template-ligand conjugate of claim 2, wherein the first ligand is attached to the N-terminal amino acid residuel of one of the three polypeptide chains.

4. The template-ligand conjugate of claim 3, wherein the C-terminal amino acid residue of each of the three polypeptide chains is covalently bonded to a tri-crosslinker.

5. The template-ligand conjugate of claim 4, further comprising a second biologically active ligand and a third biologically active ligand, wherein the first, second, and third ligands are attached to the template via covalent bonding with the N-terminal amino acid residues of the three polypeptide chains, respectively.

6. The template-ligand conjugate of claim 5, wherein the three polypeptide chains are identical.

7. The template-ligand conjugate of claim 6, wherein the three polypeptide chains each contain tripeptide repeat sequence aligned to form a triple helix coil.

8. The template-ligand conjugate of claim 1, wherein the repeat sequences are located in the C-terminal region of each of the three polypeptide chains.

9. The template-ligand conjugate of claim 8, wherein the first ligand is attached to the C-terminal amino acid residue of one of the three polypeptide chains.

10. The template-ligand conjugate of claim 9, wherein the N-terminal amino acid residue of each of the three polypeptide chains is covalently bonded to a tri-crosslinker.

11. The template-ligand conjugate of claim 10, further comprising a second biologically active ligand and a third biologically active ligand, wherein the first, second, and third ligands are attached to the template via covalent bonding with the C-terminal amino acid residues of the three polypeptide chains, respectively.

12. The template-ligand conjugate of claim 11, wherein the three polypeptide chains are identical.

13. The template-ligand conjugate of claim 12, wherein the three polypeptide chains each contain tripeptide repeat sequences aligned to form a triple helix coil.

14. The template-ligand conjugate of claim 1, wherein each of the three polypeptide chains, independently, has repeat tripeptide sequences of the following formula:

$$(AA^1\text{-}AA^2\text{-}AA^3)_m$$

wherein each $AA^1$, independently, is Gly, or D- or L-Ala; each $AA^2$, independently, is D- or L-Pro; each $AA^3$, independently, is D- or L-Hyp, or D- or L-Cys; and m is 4–14.

15. The template-ligand conjugate of claim 14, wherein m is 4–8.

16. The template-ligand conjugate of claim 15, wherein m is 4.

17. The template-ligand conjugate of claim 1, wherein each of the three polypeptide chains, independently, has repeat hexapeptide sequences of the following formula:

$$(AA^1\text{-}AA^2\text{-}AA^3\text{-}AA^4\text{-}AA^5\text{-}AA^6)_n$$

wherein each $AA^1$, independently, is Gly; each $AA^2$, independently, is D- or L-Pro; each $AA^3$, independently, is D- or L-Hyp, or D- or L-Cys; each $AA^4$, independently, is D- or L-Ala; each $AA^5$, independently, is D- or L-Pro; each $AA^6$, independently, is D- or L-Hyp, or D- or L-Cys; and n is 2–7.

18. The template-ligand conjugate of claim 17, wherein n is 2–4.

19. The template-ligand conjugate of claim 18, wherein n is 2.

20. The template-ligand conjugate of claim 4, wherein each of the three polypeptide chains, independently, has repeat tripeptide sequences of the following formula:

$$(AA^1\text{-}AA^2\text{-}AA^3)_m$$

wherein each $AA^1$, independently, is Gly, or D- or L-Ala; each $AA^2$, independently, is D- or L-Pro; each $AA^3$, independently, is D- or L-Hyp, or D- or L-Cys; and m is 4–14.

21. The template-ligand conjugate of claim 20, wherein m is 4.

22. The template-ligand conjugate of claim 4, wherein each of the three polypeptide chains, independently, has repeat hexapeptide sequences of the following formula:

$$(AA^1\text{-}AA^2\text{-}AA^3\text{-}AA^4\text{-}AA^5\text{-}AA^6)_n$$

wherein each $AA^1$, independently, is Gly; each $AA^2$, independently, is D- or L-Pro; each $AA^3$, independently, is D- or L-Hyp, or D- or L-Cys; each $AA^4$, independently, is D- or or L-Ala; each $AA^5$, independently, is D- or L-Pro; each $AA^6$, independently, is D- or L-Hyp, or D- or L-Cys; and n is 2–7.

23. The template-ligand conjugate of claim 22, wherein n is 2.

24. The template-ligand conjugate of claim 10, wherein each of the three polypeptide chains, independently, has repeat tripeptide sequences of the following formula:

$$(AA^1\text{-}AA^2\text{-}AA^3)_m$$

wherein each $AA^1$, independently, is Gly, or D- or L-Ala; each $AA^2$, independently, is D- or L-Pro; each $AA^3$, independently, is D- or L-Hyp, or D- or L-Cys; and m is 4–14.

25. The template-ligand conjugate of claim 24, wherein m is 4.

26. The template-ligand conjugate of claim 10, wherein each of the three polypeptide chains, independently, has repeat hexapeptide sequences of the following formula:

$$(AA^1\text{-}AA^2\text{-}AA^3\text{-}AA^4\text{-}AA^5\text{-}AA^6)_n$$

wherein each $AA^1$, independently, is Gly; each $AA^2$, independently, is D- or L-Pro; each $AA^3$, independently, is D- or L-Hyp, or D- or L-Cys; each $AA^4$, independently, is D- or L-Ala; each $AA^5$, independently, is D- or L-Pro; each $AA^6$, independently, is D- or L-Hyp, or D- or L-Cys; and n is 2–7.

27. The template-ligand conjugate of claim 26, wherein n is 2.

* * * * *